(12) United States Patent
Ozdil et al.

(10) Patent No.: US 9,370,321 B2
(45) Date of Patent: Jun. 21, 2016

(54) ULTRASOUND BASED ANTIGEN BINDING DETECTION

(75) Inventors: Deniz Ozdil, Auburn (AU); Michael Keoni Manion, Cronulla (AU); George Charles Peppou, Hornsby Heights (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 227 days.

(21) Appl. No.: 13/993,908

(22) PCT Filed: Jun. 25, 2012

(86) PCT No.: PCT/US2012/044006
§ 371 (c)(1),
(2), (4) Date: Jun. 13, 2013

(87) PCT Pub. No.: WO2014/003709
PCT Pub. Date: Jan. 3, 2014

(65) Prior Publication Data
US 2013/0345527 A1 Dec. 26, 2013

(51) Int. Cl.
*A61B 5/145* (2006.01)
*A61B 8/12* (2006.01)
*A61B 8/08* (2006.01)
*A61B 5/00* (2006.01)
*A61B 10/00* (2006.01)
*A61B 10/02* (2006.01)

(52) U.S. Cl.
CPC ......... *A61B 5/14503* (2013.01); *A61B 5/14546* (2013.01); *A61B 8/12* (2013.01); *A61B 8/52* (2013.01); *A61B 8/5223* (2013.01); *A61B 5/6848* (2013.01); *A61B 10/00* (2013.01); *A61B 10/0283* (2013.01); *A61B 2562/066* (2013.01)

(58) Field of Classification Search
None
See application file for complete search history.

(56) References Cited

U.S. PATENT DOCUMENTS

| 4,312,228 | A | | 1/1982 | Wohltjen |
| 4,735,906 | A | | 4/1988 | Bastiaans |
| 5,190,766 | A | * | 3/1993 | Ishihara ............... A61K 9/5052 424/489 |
| 5,843,109 | A | * | 12/1998 | Mehta et al. ................... 606/169 |
| 6,289,717 | B1 | | 9/2001 | Thundat et al. |
| 6,503,701 | B1 | * | 1/2003 | Bauer ............... 435/4 |
| 6,770,070 | B1 | * | 8/2004 | Balbierz .................. 606/41 |
| 6,866,670 | B2 | * | 3/2005 | Rabiner et al. ................. 606/128 |
| 7,303,530 | B2 | | 12/2007 | Barnes et al. |
| 7,927,288 | B2 | | 4/2011 | Gianchandani et al. |
| 8,062,231 | B2 | | 11/2011 | Boecker et al. |
| 2002/0011986 | A1 | * | 1/2002 | Hasegawa et al. ............ 345/108 |

(Continued)

FOREIGN PATENT DOCUMENTS

| EP | 2017613 | 7/2008 |
| WO | WO 2005/066635 | 12/2004 |
| WO | WO 2010/138871 | 5/2010 |

OTHER PUBLICATIONS

Burry, R.W., Immunocytochemistry A Practical Guide for Biomedical Research, "Chapter 2: antibodies", Springer Science+Buisness Media, LLC 2010.*

(Continued)

*Primary Examiner* — Tse Chen
*Assistant Examiner* — Joanne Hoffman
(74) *Attorney, Agent, or Firm* — The Juhasz Law Firm

(57) ABSTRACT

Embodiments provided here generally relate to combinations of ultrasound aspects and antibodies. In some embodiments, antibodies are immobilized on a surface and binding of the antibodies to antigens can be detected by detecting changes in the vibrational properties of the surface.

25 Claims, 5 Drawing Sheets

(56) References Cited

U.S. PATENT DOCUMENTS

| | | | |
|---|---|---|---|
| 2002/0026127 A1* | 2/2002 | Balbierz | A61B 18/1206 600/567 |
| 2002/0142388 A1* | 10/2002 | Chen | 435/69.1 |
| 2002/0146702 A1* | 10/2002 | Vielkind | 435/6 |
| 2003/0068636 A1* | 4/2003 | Veiby | 435/6 |
| 2004/0038321 A1* | 2/2004 | Charrier | 435/7.23 |
| 2004/0220753 A1* | 11/2004 | Tabe | 702/32 |
| 2007/0191733 A1* | 8/2007 | Gianchandani et al. | 600/564 |
| 2009/0220382 A1* | 9/2009 | Palena et al. | 422/68.1 |
| 2010/0088039 A1 | 4/2010 | Yang et al. | |
| 2010/0256597 A1* | 10/2010 | Prausnitz | A61F 9/0017 604/506 |
| 2011/0248700 A1 | 10/2011 | Huber et al. | |
| 2011/0257029 A1* | 10/2011 | Haab et al. | 506/9 |

OTHER PUBLICATIONS

International Search Report and Written Opinion dated Sep. 24, 2012 in International Application No. PCT/US2012/044006, filed on Jun. 25, 2012.

Kumar, "Biosensors Based on Piezoelectric Crystal Detectors: Theory and Application," JOM-e, 2000, 9 pages, vol. 52 (10).

Li et al., "A Bulk PZT Microsensor for In-Situ Tissue Contrast Detection During Fine Needle Aspiration Biopsy of Thyroid Nodules," Department of Internal Medicine, Division of Metabolism, Endocrinology & Diabetes, University of Michigan, Ann Arbor, Michigan.

Li et al., "An Active Tissue-Contrast Sensing Microsystem for Biopsy Needles: Initial Results," IEEE, Jan. 23-27, 2011, pp. 21-24.

Suri et al., "Activating Piezoelectric Crystal Surface by Silanization for Microgravimetric Immunobiosensor Application," Biosensors & Bioelectronics, 1996, vol. 11, No, 12, pp. 1199-1205.

Suri et al., "Determination of Immunoglobulin M Concentration by Piezoelectric Crystal Immunobiosensor Coated with Protamine," Biosensors & Bioelectronics, 1994, vol. 9, pp. 325-332.

Wang et al., "A Reusable Piezo-Immunosensor with Amplified Sensitivity for Ceruloplasmin Based on Plasma-Polymerized Film," Talanta, 2004, vol. 62, pp. 201-208.

* cited by examiner

ULTRASOUND BASED ANTIGEN BINDING DETECTION

CROSS-REFERENCE TO RELATED APPLICATIONS

This application is the U.S. National Stage entry under 35 U.S.C. §371 of International Application No. PCT/US2012/044006, filed Jun. 25, 2012, the contents of which are hereby incorporated by reference in its entirety.

FIELD

Embodiments provided here generally relate to combinations of ultrasound aspects and antibodies.

BACKGROUND

Ultrasound techniques can be used for obtaining images in a variety of technologies. For example, endoscopic ultrasound (EUS) provides a powerful imaging modality and can be used in medical procedures to image various internal organs and structures.

SUMMARY

In some embodiments, an endoscopic ultrasound (EUS) probe is provided. The device includes a piezoelectric surface and at least one antibody immobilized on the piezoelectric surface.

In some embodiments, a method of detecting the presence of an antigen is provided. The method can include providing an endoscopic ultrasound probe that includes a piezoelectric surface and at least one antibody immobilized on the piezoelectric surface. The method can include stimulating the endoscopic ultrasound probe with at least one ultrasound wave. The method can include detecting a change in vibration frequency of the piezoelectric surface upon binding of an antigen to the at least one antibody.

In some embodiments, an aspiration needle is provided. The needle includes a piezoelectric material and at least one antibody on the piezoelectric material.

In some embodiments, a kit is provided. The kit can include at least one ultrasound transducer, at least one fine-needle aspirator needle, at least one piezoelectric material, and at least one antibody.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
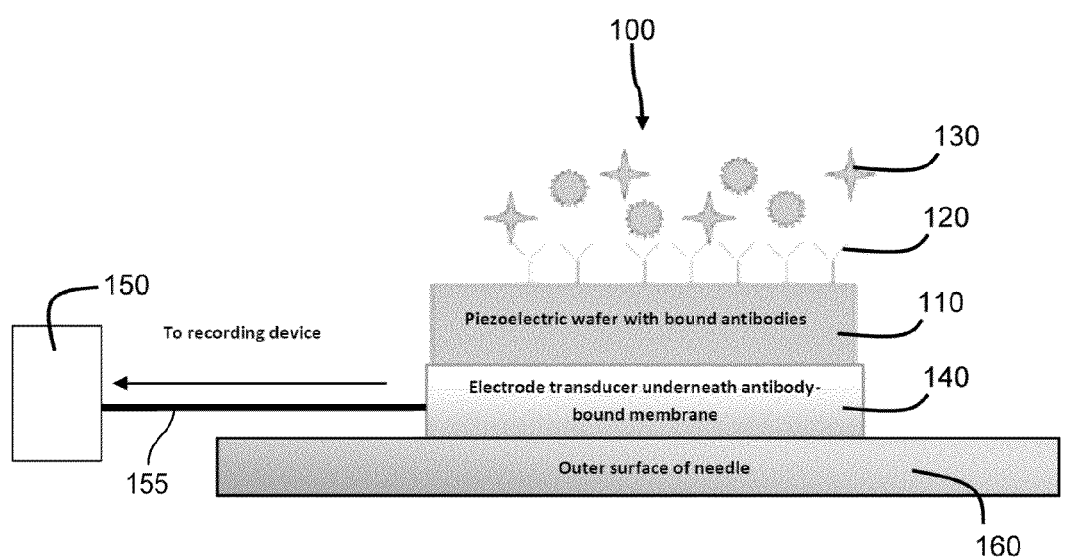
FIG. 1 is a drawing that depicts some embodiments of an endoscopic ultrasound probe.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Provided herein are embodiments that relate to the combination of ultrasound equipment and antibodies and/or antibody binding fragments. As described herein, it has been appreciated that one can combine one or more of the benefits of an ultrasound device, with one or more benefits of antibody based detection. For example, while ultrasound can deliver useful image based information regarding the surroundings of the probe, it traditionally lacks the ability to provide information on the molecular level. In contrast, antibodies can provide information on a molecular level. Not only does the combination of the two techniques allow for greater information and convenience, but some such combinations offer even greater benefits. For example, in some embodiments, the antibodies can be associated with a piezoelectric surface. Such a surface can respond to ultrasound energy by vibration and generate an electrical signal in response to the ultrasound signal that corresponds to the vibration generated. As binding of a target to the antibody can alter the vibration properties of the piezoelectric surface, this alteration can be used to determine whether or not a target molecule has been bound by the antibody. Thus, an ultrasound device can be used to not only obtain ultrasound information regarding the environment, but can also be used to detect binding of antigens by antibodies on a piezoelectric surface.

In some embodiments, an ultrasound probe is provided. The probe can include a piezoelectric surface and at least one antibody immobilized on the piezoelectric surface.

FIG. 1 illustrates some embodiments of an antibody probe 100. The antibody probe can include a piezoelectric surface 110 and one or more antibodies 120 immobilized on the piezoelectric surface. In some embodiments, the antibodies 120 can bind specifically to tissue-specific antigens 130. The antibody probe 100 can include an electrode transducer 140. The electrode transducer can be in electrical and/or data communication with a recording device 150 via, for example a lead or wire 155. Optionally, the antibody probe can be positioned on the outer surface of a needle 160, for example an aspiration needle. The electrode transducer 140 can be positioned underneath the piezoelectric surface (for example, the transducer can be positioned between the piezoelectric surface and the outer surface of the needle).

As noted above, the electrode transducer allows for changes in the vibrations of the piezoelectric surface 110, provided by changes in the electrical properties of the piezoelectric surface, to be communicated to other devices, such as the recording device 150 in FIG. 1.

Figure 2A:
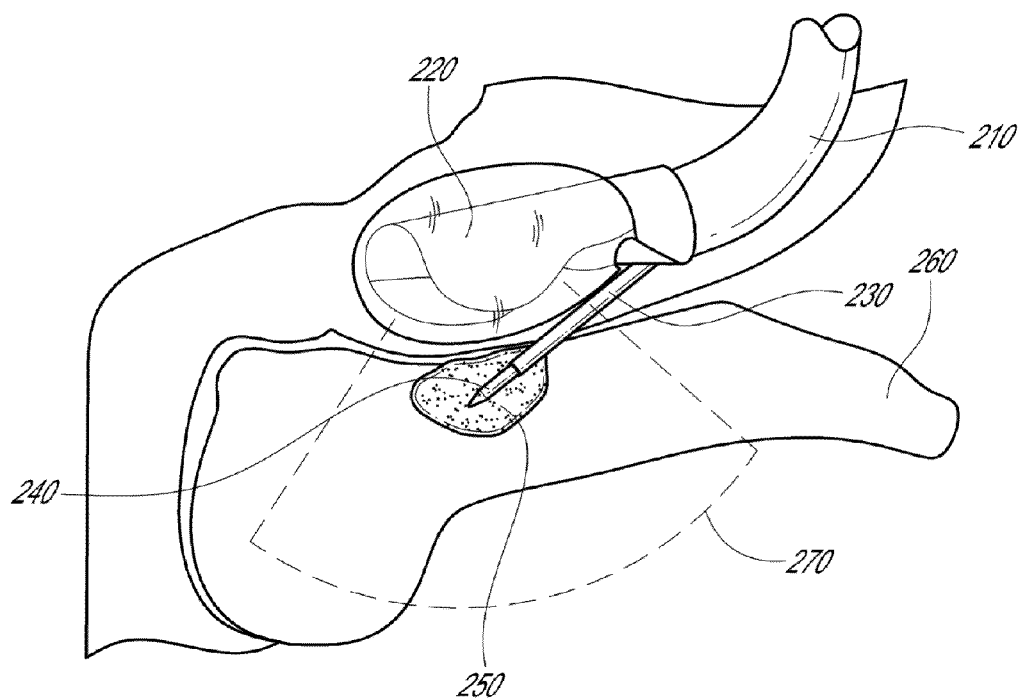
FIG. 2A is a drawing that depicts some embodiments of an endoscopic ultrasound probe positioned in a tissue.

FIG. 2A illustrates some embodiments of an endoscopic ultrasound probe, which includes the antibody probe, positioned in a tissue. An endoscope 210 includes an ultrasound head 220 on a first end of the endoscope. Optionally, the first end of the endoscope is also connected to a biopsy needle, for example an aspiration needle 230. The antibodies 240 can be placed anywhere on the probe or on a part associated with the probe, such as the needle 230 or other surface. The placement of the antibodies 240 on the needle 230 allows for immediate testing of the sample 250 surrounding the needle. Furthermore, the placement of the antibodies 240 proximally to the needle, allows one to test the local molecular environment for specific markers and then take a biopsy of the region of interest or tissue of interest 260 via the needle 230. While not shown in FIG. 2A, the antibodies can be on top of a piezoelectric surface and electrode transducer, as shown in FIG. 1 (even if not located on the needle). Furthermore, while the antibodies are shown as being on the needle 230, one of skill in the art will appreciate that the antibodies can be on any location that is part of or separate from the ultrasound device, as long as ultrasound energy can be supplied to the piezoelectric surface to create the vibration in the piezoelectric surface. The energy can be from an ultrasound device, in which case, the antibodies and the piezoelectric surface should be positioned appropriately so that the piezoelectric surface can receive the ultrasound energy 270.

Figure 2B:
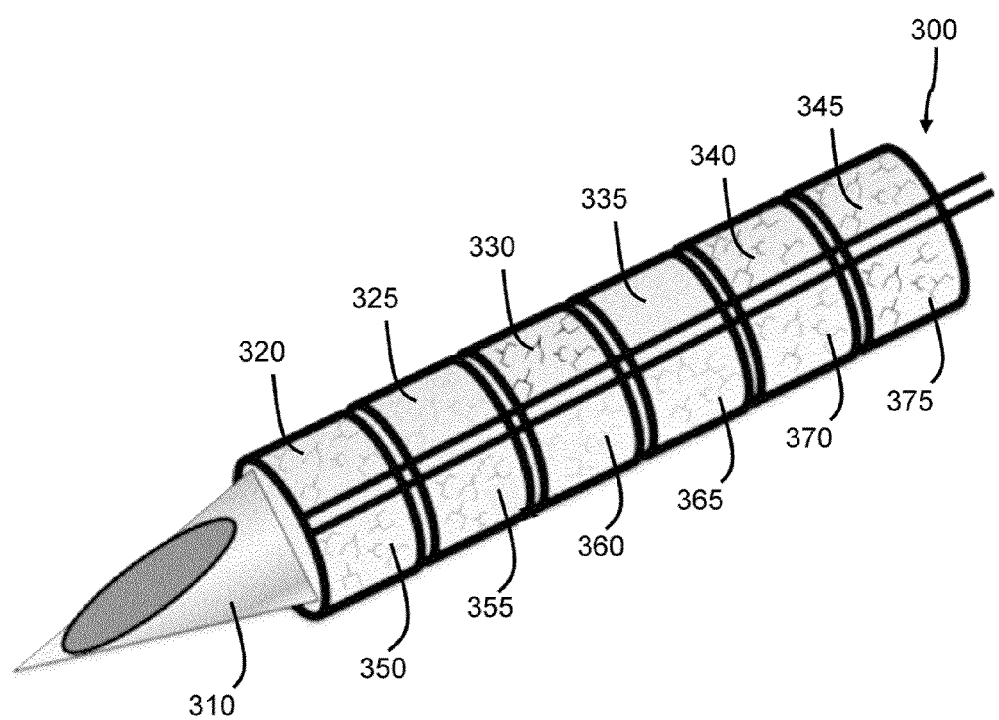
FIG. 2B is a drawing that depicts some embodiments of an endoscopic ultrasound probe that includes a needle.

While not the only embodiment envisioned, FIG. 2B illustrates an endoscopic ultrasound probe needle 310 with an array of antibody probe zones on it. The antibody probe 300 includes a first surface 320 on which a first antibody can or is immobilized, and a second surface 325 on which a second antibody can or is immobilized. The probe can include additional surfaces (a third surface 330, a fourth surface 335, a fifth surface 340, a sixth surface 345, a seventh surface 350, an eighth surface 355, a ninth surface 360, a tenth surface 365, an eleventh surface 370, a twelfth surface 375, etc.), and an additional antibody or antibody type (for example, an antibody that binds to a specific protein) can be immobilized on each surface. The first 320, second 325, third 330, fourth 335, fifth 340, sixth 345, seven 350, eighth 355, ninth 360, tenth 365, eleventh 370, and twelfth 375 surfaces can be arranged in a systematic pattern; however, they can also be different in shape and arranged randomly. In the depicted embodiment, when a single type of antibody is associated with each surface area or zone, one can effectively provide an array of sensing zones. That is, if the antibodies of surface 320 bind to protein X and antibodies of surface 325 bind to protein Y, the device can be used to detect the presence and/or absence of protein X and/or Y and to distinguish between the two antigens. For example, a change in electrical signal of surface 320, without a change in signal from surface 325 can indicate the presence of protein X and the absence of protein Y. If changes in electrical signals from both surfaces occur, then both proteins X and Y can be present (or that some other change in binding activity has occurred regarding the antibodies in each of the two zones).

As shown in FIG. 1, the piezoelectric surface can include a single layer of a material; however, the piezoelectric surface can also include two or more layers of material. Any range of thickness can be used for the piezoelectric surface, for example, about 1 micrometer to about 5000 micrometers.

For the sake of brevity, the term "antibody" is used to denote both complete antibodies and binding fragments thereof. Thus, unless otherwise specified, any disclosure regarding antibodies also encompasses the option of binding fragments of antibodies (including antibody fragments such as antigen-binding fragments (Fab), single chain variable fragments (scFv), third generation (3G), etc.). The antibody can be immobilized on the piezoelectric surface by at least one of a covalent bond, crosslinking, a linker molecule, for example a peptide or a second antibody, electromagnetic force, or it can be embedded in the surface.

The surface can include two or more antibodies that respectively bind specifically to two or more different antigens. The surface can include two or more antibodies that respectively bind to different epitopes of the same antigen. The antibodies can be arranged and/or isolated such that specific antibodies are associated with specific areas of the piezoelectric surface (such that a signal generated from the piezoelectric surface can be correlated back to a specific type of antibody and thus the presence of a specific target molecule. The antibodies can also be randomly distributed such that one only knows that at least some antibody directed target antigen is present in the environment, but not necessarily which exact molecule.

The piezoelectric surface can include a crystal. The piezoelectric surface can be crystalline. The piezoelectric surface can include a non-crystalline material, for example polyvinylidene fluoride (PVDF), or piezoelectric ceramic material. Any material that is able to convert vibrational frequency to an electrical signal (either directly or indirectly) can be used to monitor the bound or unbound state of the antibodies on the surface.

The probe can include an electrode in electrical communication with the piezoelectric surface. The electrode can be an ultrasound transducer. The electrode can be positioned beneath the piezoelectric surface as described herein. The electrode can be configured to detect a change in piezoelectric activity. In some embodiments, a synthetic piezoelectric material can be used for the electrode (e.g. PVDF, synthetic crystal or ceramic material). The electrode can be configured to distinctly detect a change in piezoelectric activity for two or more areas of the piezoelectric surface. Thus, multiple, electrically isolated electrodes can be present, such as a separate electrode under each surface shown in FIG. 2B. The probe can include two or more electrodes. The probe can include a first electrode and a second electrode that are each positioned beneath the same area of the piezoelectric surface (for example a primary and a backup electrode). The probe can include a first electrode positioned beneath a first area of the piezoelectric surface, and a second electrode positioned beneath a second area of the piezoelectric surface. The probe can include additional electrodes, each positioned beneath an additional area of the piezoelectric surface.

The device can include a processor in data communication with the electrode. The electrode can be in data communication with the processor via a data cable connecting the electrode to an input of the processor. The electrode can be in data communication with the processor via an electrical lead connecting the electrode to an output or input/output of the processor. The electrode can be in data communication with the processor wirelessly.

In some embodiments, the first antibody specifically binds to a first antigen, and the second antibody specifically binds to a second antigen. The second antigen can be different from the first antigen. The first, second, and each of the additional antibodies can specifically bind to a different antigen than the other antibodies. The first antibody can specifically bind to a first epitope of the first antigen, and the second antibody specifically binds to a second epitope of the first antigen. The first antigen can include a first tissue-specific antigen, and the second antigen can include a second tissue-specific antigen. The first tissue-specific antigen and the second tissue-specific antigen can be typically present in the same tissue. In some embodiments, the first tissue-specific antigen and the second tissue-specific antigen are not typically found at detectable levels in the same tissue. The antigen can be a tissue-specific antigen. The second antibody can bind to the same epitope as the first antibody, and/or is a clone of the first antibody, and thus provides a replicate of the binding activity of the first antibody (e.g. for detecting the binding activity of the first antibody in duplicate).

A first quantity of the first antibody can be immobilized on the first surface, and a second quantity of the first antibody can be immobilized on the second surface. Additional quantities of the first antibody can be immobilized on additional surfaces. The different quantities of the first antibody on different surfaces can recognize different concentrations of antigen. Different quantities of the first antibody on different surfaces can increase the sensitivity range of the probe.

In some embodiments, at least one of the additional antibodies binds to a different epitope as the first and second antibody. One or more of the second antibody and/or the additional antibodies can bind to an antigen that is non-tissue-specific, or ubiquitous in the tissue or tissues to be probed (e.g. immunoglobulin of the species being probed), thus providing a "positive control antibody". The positive control antibody can bind specifically to an antigen that is tissue-non-specific ("tissue-non-specific marker," e.g. albumin, LDH, muscle markers when muscle is probed, liver markers when liver is probed, etc). At least one of the second antibody or the additional antibodies can bind to an antigen that is not naturally found in any of the tissue or tissues to be probed, or contains a mutation (for example, at least one of a point mutation, insertion, or deletion) that interferes with the binding of the antibody to an antigen, thus providing a "negative control antibody."

The antibody can be monoclonal. The antibody can be from a mammalian host, for example goat, sheep, camel, horse, donkey, cow, pig, rabbit, mouse, rat, hamster, guinea pig, and human. The antibody can be from an avian host, for example chicken. The antibody can be a shark (IgNAR) single domain antibody. The antibody can be chimeric. A mixture of antibodies from two or more hosts can be provided. The antibody can include at least one region of an antibody from a first host, and the remaining regions are from a second host. The "region" from the first host can be at least one of the following: Fc, Fab, CH2, CH3, heavy chain CDR1, heavy chain CDR2, heavy chain CDR3, light chain CDR1, light chain CDR2, light chain CDR3, heavy chain variable region, light chain variable region, heavy chain FR1, heavy chain FR2, heavy chain FR3, heavy chain FR4, light chain FR1, light chain FR2, light chain FR3, and/or a light chain FR4, and the "regions" not from the first host can be from the second host. In some embodiments, one or more of the CDRs is from a first host (e.g., 1, 2, 3, 4, 5, or 6 of the CDRs are from the first host). The antibody can include a heavy chain from a first host. The antibody can include at least one of a heavy chain framework region 1, a heavy chain framework region 2, a heavy chain framework region 3, a heavy chain framework region 4 from the first host. The antibody can include a constant domain from the first host. The antibody can include a variable domain from the first host. The antibody can include a constant domain and a variable domain from the first host. The antibody can include at least one of a heavy chain framework region 1, heavy chain framework region 2, heavy chain framework region 3, heavy chain framework region 4, constant domain, or variable domain from the second host. The antibody can be humanized, and contains at least one region from a human host. The antibody can be a humanized antibody with 1, 2, 3, 4, 5, or 6 CDR's from a non-human host.

The antibody can be an IgY antibody. The antibody can be an IgM antibody. The antibody can be an IgA antibody. The antibody can be an IgG antibody. The antibody can be an IgE antibody. The antibody can be an IgD antibody. The term "antibody" encompasses antibody mimetics and/or engineered antibodies, including, but not limited to Small Modular ImmunoPharmaceuticals ("SMIPs"), Fab, F(ab')2 Fab', scFv, di-scFv, etc.

The isolated antibody can be in a substantially pure form. In some embodiments, the isolated antibody is separate from any cells.

Antibodies can be selected to bind to desired targets. Thus, any antibody can be used, and the specific antibody can be selected based upon the use of the probe and/or what one wishes to be able to detect via the antibody. In some embodiments, the antibody binds to a tissue-specific antigen, which provides a tissue specific marker. The antibody can bind to a tissue-non-specific antigen, which provides a tissue-non-specific marker. The appropriate tissue-specific marker and/or tissue-non-specific marker can be selected based on the identity of the tissue being probed and/or biopsied. A tissue-specific marker can include an antigen present in the tissue being biopsied, but not present, or present in substantially lower concentrations in tissue surrounding the tissue being biopsied. For example, a tissue-specific marker can include a cancer cell marker.

In some embodiments, a tissue non-specific marker can include an antigen present in the tissue being biopsied, and in tissue surrounding the tissue being biopsied. For example, for a tissue-non-specific antigen can include an albumin, an albumin fragment, or lactose dehydrogenase (LDH), or a marker found throughout the organ or tissue being probed (e.g. muscle-specific markers when muscle is being proved). The antigens can be extracellular markers, for example molecules immobilized on the surfaces of cells, molecules in the extracellular matrix, or molecules secreted by cells. Different antibodies, each of which is specific to a different maker in the same tissue, or a different epitope of the same marker can be employed, for example to increase the sensitivity and robustness of detection. For example, different monoclonal antibodies to different markers of the same tissue can be provided. In some embodiments, each type antibody is immobilized on a different area of the piezoelectric surface. In some embodiments, the antibodies can bind to a general class or type of epitope. In some embodiments, the first antigen bound by the first antibody is a different antigen from the second antigen that is bound by the second antibody. In some embodiments, the absence of a particular antigen within a subject can be used to assist in diagnosing the subject.

As shown in FIGS. 2A and 2B, the antibodies can be associated with the surface of an FNA needle. The needle can be sterile and/or packaged separately from an ultrasound device. The needle can be any size, for example, no larger in gauge than 12G. The needle can be about 18G to 23G. The needle can be a fine needle aspiration needle. While not limited in size, the needle can have a gauge from 12G to 30G. The antibody and/or the piezoelectric surface and/or electrode can all be part of the surface of the needle (and thus, the needle can have electrical leads for communication with other electrical devices). The antibody and/or the piezoelectric surface and/or electrode can all be part of any other surface of the ultrasound device and/or be on a separate device that can be positioned independently of the ultrasound device.

In some embodiments, a method of detecting the presence of an antigen is provided. The method can include providing an EUS probe that includes at least one antibody immobilized on a piezoelectric surface as described herein. The method can include stimulating the EUS probe with at least one ultrasound wave and detecting a change in vibration frequency of the piezoelectric surface upon the binding of an antigen to the antibody. One can also combine this with performing an ultrasound of the surrounding tissue, such that one obtains and can map the antibody based data with the structures obtained via the ultrasound. In some embodiments, one can use the ultrasound information to guide one to a specific structure or location, in which the antibody based probe can be used.

Figure 4:
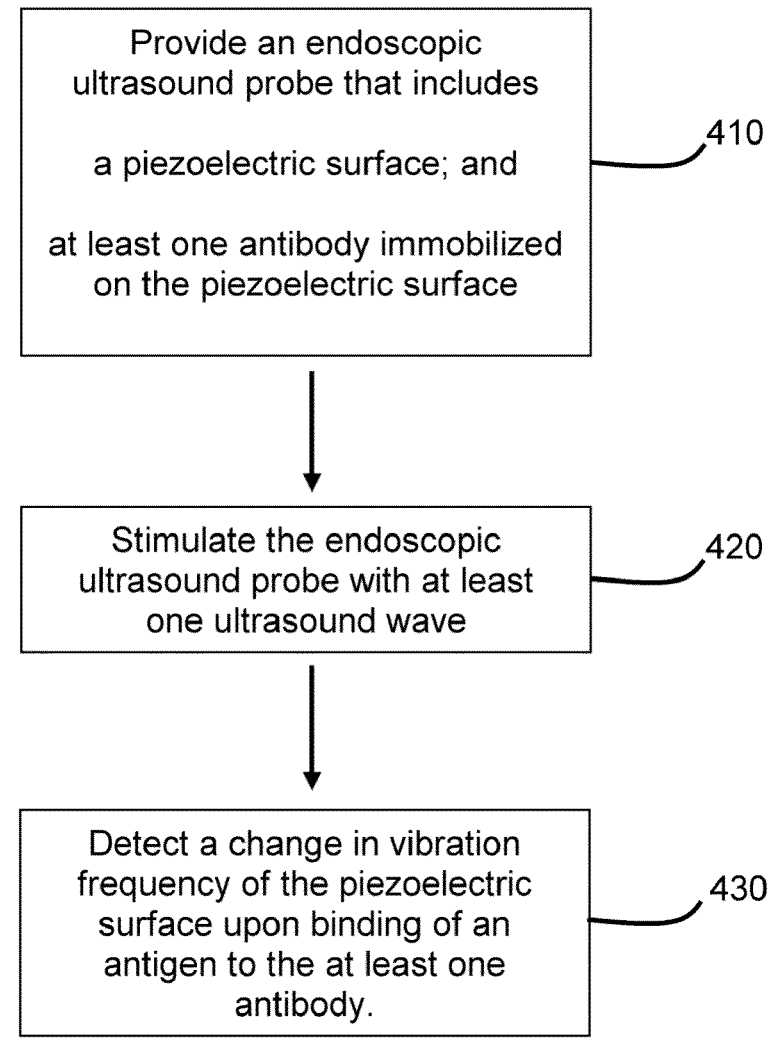
FIG. 4 is a flow diagram illustrating some embodiments of a method of detecting the presence of an antigen.

FIG. 4 is a flow diagram illustrating some embodiments of a method of detecting the presence of an antigen. An endoscopic ultrasound probe that includes a piezoelectric surface and at least one antibody immobilized on the piezoelectric surface can be provided 410. The endoscopic ultrasound probe can be stimulated with at least one ultrasound wave 420. A change in vibration frequency of the piezoelectric surface, upon binding of an antigen to the at least one antibody, can then be detected 430. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. In some embodiments, all that need be stimulated is the piezoelectric surface, so that changes in the vibrational frequency of the surface (due to binding of a target molecule to an antibody associated with the surface) can be detected. Optionally, before, during, or after the antibody based detection, one can obtain ultrasound information of the surrounding tissue and correlate it with the antibody based information.

The method can include stimulating the ultrasound probe with at least one ultrasound wave. The ultrasound probe can be stimulated at a frequency of at least about 0.1 MHz, for example, between about 0.1 MHz and about 50 MHz. The ultrasound probe can be stimulated at a surface intensity of at least about 0.5 mW/cm$^2$. The antibody covered section can be stimulated for a duration of at least about 0.1 µs, for example at least about 0.1 µs to 10 or more seconds. The stimulation may be conducted at intervals, thereby monitoring mass changes at discrete times. The stimulation can provide continuous excitation, monitoring for seconds to several minutes, monitoring mass changes during this time. The stimulation can be provided by an ultrasound transducer.

The method can include detecting a change in vibration frequency of the piezoelectric surface upon binding of an antigen to the antibody immobilized on the piezoelectric surface. For example, in embodiments in which two or more antibody molecules are immobilized on an area of a piezoelectric surface, binding the antibody to an antigen includes binding at least 20% of the antibody molecules immobilized on a surface to an antigen.

The change of the piezoelectric surface can be compared to the frequency change of a surface on which a negative control antibody is immobilized as described herein (e.g. a surface having a bound antibody for an antigen not present in humans. Such a negative control can indicate non-specific binding), and the fractional frequency change can be calculated. The frequency change for the piezoelectric surface can be compared to the frequency change of a surface on which a positive control antibody is immobilized as described herein (e.g. a surface having an antibody known to be bound to its antigen), and the fractional frequency change can be calculated. In some embodiments, the frequency change for the piezoelectric surface can be compared to the frequency change of both a positive control surface as described herein and a negative control surface as described herein.

Detecting a change in vibration frequency can include determining a first vibration frequency of the piezoelectric surface when no antigen is bound to the at least one antibody and determining a second vibration frequency of the piezoelectric surface when an antigen is bound to the at least one antibody.

The vibration frequency can be monitored in real time. An electrode as described herein can be used to measure the vibration frequency of a piezoelectric surface (via the electrical signal generated from the piezoelectric surface). The vibration frequency can be communicated to a processor, which produces an output corresponding to a vibration frequency. Vibration frequencies can be measured in real time, and binding rates of antibodies to antigen can be calculated using a curve-fitting algorithm.

The antibody can bind specifically to the tissue-specific antigen, and the method can include binding of the antibody to a tissue-specific antigen. Multiple antibodies that bind specifically to the same tissue-specific antigen can be immobilized on an area of the piezoelectric surface. A positive binding threshold or "positive detection event" can be set as desired, for example, when about 20% of the antibody molecules are bound to the tissue-specific antigen. The threshold can depend upon the amount of target molecule that should be present and the binding ability of the antibody itself.

While not needed for all situations, it can be useful to have a baseline level of electrical activity or control level of activity in order to determine if and how much, binding has occurred. Obtaining such a baseline can include allowing the binding of the first antibody to a tissue-specific antigen and also obtaining an electrical signal when the first antibody is bound or is not bound to the tissue-specific antigen. The bound and unbound electrical signals can be compared in order to determine how the change in presence or absence of a target translates into a change in electrical signal. In some situations, a contemporaneous comparison between two or more surface areas can be useful, for example, a first antibody can bind to the tissue-specific antigen at the first surface area while a second antibody, in a second area, may or may not bind to the molecule. The second antibody can be a negative control, where the antibody should not bind to the target molecule. The second antibody can be a positive control antibody, where it will bind to the target molecule. These comparisons can allow one to obtain a clearer reading to verify that the change in electrical signal is indeed due to changes in specific binding by the antibodies, or some other effect. A vibration frequency of the second surface can be detected when the second antibody is not bound to an antigen. Binding of the first antibody to the tissue-specific antigen can be inferred by comparing the vibration frequency of the first surface to the vibration frequency of the second surface, in view of whether the second surface is known to be bound (e.g. positive control) or not bound (e.g. negative control) to an antigen.

The vibration frequency of the first surface and second surface can be determined at substantially the same time. The vibration frequency of the second surface can be determined first (e.g. a calibration step), and the vibration frequency of the first surface can be subsequently determined.

The method can include binding the antibody to a tissue-non-specific marker, as described herein. The tissue-non-specific marker can include, as non-limiting examples, an albumin, an albumin fragment, or lactose dehydrogenase (LDH).

In some embodiments, an aspiration needle is provided. The aspiration needle can include a piezoelectric surface, for example a piezoelectric crystal, on a surface of the aspiration needle; and at least one antibody on the piezoelectric surface. In some embodiments, the antibody can be covalently connected to the surface.

The aspiration needle, or aspirator, can include a piezoelectric surface immobilized on the surface of the needle, and at least one antibody immobilized on the piezoelectric surface. The piezoelectric surface can include a piezoelectric crystal or other material that converts vibrational energy to electrical energy. The piezoelectric crystal can be immobilized on a surface of the needle. The piezoelectric crystal can be directly covalently bonded to the surface of the needle. The piezoelectric crystal can be bonded to the surface of the needle via an adhesive. The piezoelectric crystal need not be bonded to the surface of the needle, but can be attached mechanically.

The antibody can bind specifically to an extracellular marker. The extracellular marker can be a tissue-specific marker. The extracellular marker can be a tissue-non-specific marker as described herein.

The fine needle aspirator can include a first antibody immobilized on a first area of the piezoelectric surface as described herein, and a second antibody immobilized on a second area of the piezoelectric surface as described herein. The fine needle aspirator can include additional antibodies immobilized on additional areas of the piezoelectric surface as described herein. FIG. 2B illustrates an embodiment of a fine needle aspirator with twelve areas of a piezoelectric surface, each area can have an antibody that binds specifically to a different molecular target immobilized on it.

The first area, second area, and any additional areas of the piezoelectric surface can be positioned in an ordered array. FIG. 2B illustrates some embodiments of an ordered array. The ordered array can include continuous cells, each cell having antibodies immobilized on it. The ordered array can include cells separated by spaces that do not have antibody immobilized on them. The first area, second area, and any additional areas of the piezoelectric surface can be positioned in a random pattern on the piezoelectric surface. The fine need aspirator needle can include a third antibody configured to bind specifically to the first antigen, and the third antibody can be immobilized on a third area of the piezoelectric crystal. In some embodiments, the third antibody binds to the same epitope of the first antigen as the first antibody. In some embodiments, the third antibody binds to a different epitope of the first antigen than the first antibody. In some embodiments, the third antibody is present in the same quantity as the first antibody, as described herein. In some embodiments, the third antibody is present in a different quantity than the first antibody, as described herein. For example, the third antibody can be used increase the robustness or sensitivity for detecting the antigen.

The needle can be configured to be reversibly attached and removed from a surface of the endoscopic ultrasound probe. The needle can be configured to attach to the endoscopic ultrasound probe via a screw, a nipple, a friction mount, or an adhesive. The needle can be disposable.

In some embodiments, kits are provided. The kit can include an ultrasound transducer, a fine-needle aspirator needle, and a piezoelectric material. The kit can include at least one antibody. The kit can include an ultrasound transducer, a fine-needle aspirator needle, a piezoelectric material, and, optionally, an antibody. The antibody can be immobilized on the piezoelectric material.

The device and/or methods provided herein can be used to identify and stage cancers on organs in the sub-thoracic cavity EUS can be enhanced to allow for the accurate, real-time characterization of lesions. It can provide an EUS technology that is able to quickly and accurately distinguish healthy tissue from abnormal tissue, and further go on to characterize the abnormal tissue. For cancerous lesions, early detection and accurate staging of cancers with such a technology can reduce costs associated with end-stage cancer medical treatment and also improve the patient quality of life. In some embodiments, the antibody or antibodies selected can bind to an antigen that would be useful in one or more blood drawn test. Antibodies can be employed that allow for detection of antigens that are normally examined in one or more blood drawn test. Thus, the presence of the antibody on the needle can allow one to assay a subject's blood for one or more antigen, without having to withdraw the blood and/or blood sample from the subject. Similarly, the absence of binding of an antigen to such an antibody can allow one to determine that the subject lacks such antigens in the tested area.

In some embodiments, a piezoelectric membrane that contains immobilized antibodies to specific tissue markers, coats the outer surface of the fine needle aspirator component of an EUS probe. The piezoelectric membrane can be arranged in an array where each unit of the array contains not only the piezoelectric crystals but also antibodies for a specific tissue marker. These markers can include soluble proteins excreted by the tissue. Each unit is dedicated to the detection of one particular marker or a group of related markers. There are also positive and negative reference units. The crystals in the membrane units can vibrate at known frequencies under stimulation from ultrasound wave from the EUS probe's own ultrasound transducer. Upon the binding of an antigen, the vibration frequency of the unit can change, which can be detected by electrodes that are between the membrane and the fine needle aspirator outer surface. The electronic signals can be registered at an ex vivo processor which computes signals from all units and produces a screen output. This mass-based immunosensor can thus characterize, in real-time, the tissue that is queried, whilst allowing the normal operation of current EUS including fine needle aspiration biopsy.

The electrodes of each membrane unit can be manufactured directly on to the needle aspirator to become one unit. Thus upon the use of the needle to retrieve a biopsy sample, the immunological detection mechanism provides pre-biopsy information about the tissue source of the sample. This method of pre-characterization of the tissue can be used to supplement the results of the biopsy giving assurance to the endoscopist of the correct positioning of the FNA needle. This can be useful confirmatory information, for example, when multiple lesions are observed, and the endoscopist chooses to sample a subset thereof. The probe can also be used to navigate margins of a lesion that the clinician has determined to be cancerous as multiple injections with the needle can be made without aspirating a biopsy sample until a positive indication is received through the probe. In some embodiments, there may be a wash step in between such measurements, which can be achieved by retracting the probe internally into the structure, and providing it with high ionic strength solution to remove all bound antigen. This wash step can optionally be monitored in real time to ensure sufficient regeneration of the probe surface. In some cases, the probe is merely switched for a new probe before reinserting.

Many sorts of piezoelectric immunosensor membranes have previously been microfabricated to sizes that can be suitable for this application. Membranes of this scale can be stimulated by a small amount of ultrasound stimulation for a decent and constant vibration frequency to be maintained.

The 7-12 MHz ultrasound frequencies of ultrasound probes can be sufficient for adequate stimulation of such a membrane.

As noted above, the array can have more than one unit functionalized in the same manner in order to provide for better statistical power. These repeated units can be placed randomly on the array in order to account for any location differences which may occur. The raw data is indicative of the increase in the mass density of a particular unit in relation to the amount of specific binding of antigen to antibodies. The non-specific binding can be accounted for by at least one unit of the array being functionalized with an equivalent amount of non-specific antibody or de-functionalized antibody. In some embodiments, in order to provide a meaningful signal, at least one unit of the array is typically functionalized with an equivalent amount of antibody specific for a known antigen in abundance in the tissue of interest, such as albumin. This can be particularly useful when determining whether the probe has been saturated with antigen. The data can be normalized using these control signals.

The binding of the antibodies can be monitored in real time, and measurements taken of the rate of binding, utilizing curve fitting algorithms. Alternatively, absolute levels of binding can be determined by determining the relative mass changes in each unit after a particular amount of time after being inserted into the tissue within the ultrasound window. Comparison of each unit, or group of related units to each other, as well as with the positive and negative controls, gives an indication of the binding of particular antigens has occurred to different units, and can be used therefore, to characterize the tissue it is inserted into. In some embodiments, statistical analysis is performed to determine whether the signals received are statistically significant. Statistical analysis can also be useful to ensure proper sampling of the tissue, such as ensuring that a threshold level of binding for controls and test units has been achieved, in order to provide for correct inference about the test results.

In some embodiments, the functionalization of each array unit is done with a unique antibody, such as a monoclonal antibody to a particular epitope, or alternatively a polyclonal antibody to a particular antigen. Alternatively, in order to broaden the specificity of response, the array unit may be functionalized with a mixture of antibodies to a group of antigens. For example, a particular array unit can be functionalized with a mixture of antibodies recognizing a range of markers for a stage of cancer, disease state, or for a particular tissue type. Similarly, an array may have units which recognize different markers for the same disease state, or tissue type, in order to provide for a statistically stronger response. Different array units can be functionalized with the same type of antibody, or mixture of antibodies, but with different concentrations in order to increase the dynamic range of the probe. For example, array units for a particular marker may be functionalized with the same antibody but with orders of magnitude different amounts.

Figure 3:
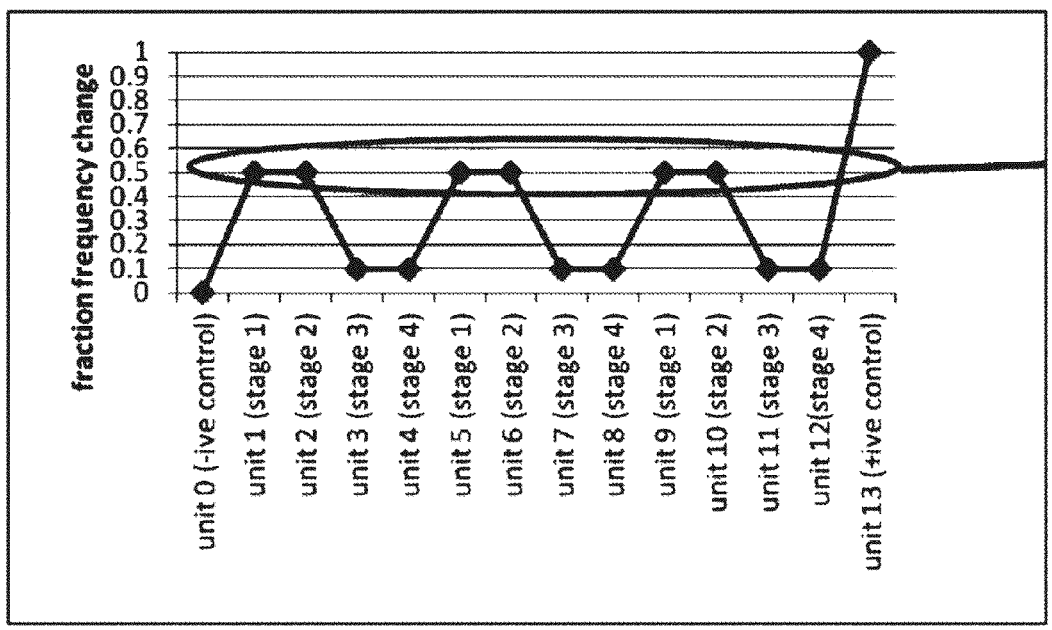
FIG. 3 is a graph that illustrates an example of the type of data output which can be received from a 14-unit sensor functionalized with antibodies recognizing markers for different stages of cancer.

FIG. 3 illustrates a simplified example of the type of data output which can be received from an embodiment of a 14 unit sensor functionalized with antibodies recognizing markers for different stages of cancer. As shown on the x-axis of the representative graph, each unit of the array is doped with antibodies that detect specific antigens or markers of a particular stage of cancer. The frequency change can be calculated as a signal relative to that of the positive and negative control units. In this example, all six array units recognizing Stage I and Stage II markers recorded a positive signal, providing a strong indication that the tissue is a Stage II tumor. This data, or a derivative thereof, can be displayed on the US screen, indicating to the endoscopist that the assay has successfully completed and recorded a statistically significant signal.

In some embodiments the piezo-membrane immunosensor—needle aspiration combination provides double confirmation of a diagnosis. The inclusion of the immunosensor provides for an intermediary process between visual analysis using EUS and a biopsy test.

Some embodiments provide real-time analysis of tissue which may have changed position from that observed in pre-operative images. By identifying changed tissue properties, some embodiments bridge a gap between selecting a region of interest as seen on the ultrasound image, and then proceeding to take a biopsy sample from this region.

Some embodiments conduct a binding assay within the ultrasound window.

While some embodiments relate to tumor staging using EUS, it can be appreciated that there are many different applications for other EUS and non-EUS applications. For example, stand-alone systems with discrete US transducers can be used in a number of biopsy settings for confirmatory results prior to obtaining the biopsy. In some embodiments, systems are designed for robust specificity and wide dynamic range, with a number of methods to provide for control, and powerful inference.

Example 1

A piezoelectric crystal having an average thickness of about 200 micrometers is divided into fourteen areas, which are labeled as units 0-13 for reference purposes. 1 μg of antibody is crosslinked to each of units 0-13. The antibody for each unit is a monoclonal antibody from a mouse host, and has an IgG isotype. The antibody crosslinked to unit 13 is an anti-human LDH antibody, and is provided as a positive control antibody. The antibody crosslinked to unit 0 is an anti-luciferase antibody, and is provided as a negative control. The antibody crosslinked to units 1, 5, and 9, binds specifically to a marker of stage 1 hepatocellular carcinoma. The antibody crosslinked to units 2, 6, and 10 binds specifically to a marker of stage 2 hepatocellular carcinoma. The antibody crosslinked to units 3, 7, and 11 binds specifically to a marker of stage 3 hepatocellular carcinoma. The antibody crosslinked to units 4, 8, and 12 binds specifically to a marker of stage 4 hepatocellular carcinoma.

The piezoelectric crystal is on the outer surface of a 20G aspiration needle so that the crystal surrounds the outer surface of the needle. An electrode transducer is positioned between the crystal and the needle, and connected to a power source and processor via an electrical lead and data cable. Thus, a fine-needle aspirator is produced.

Example 2

A piezoelectric ceramic surface having an average thickness of about 500 micrometers is divided into eight areas, which are labeled as units 0-7 for reference purposes. 1 μg of antibody is crosslinked to each of units 0-7. The antibody for each unit is a humanized monoclonal antibody and has an IgG isotype. The antibody crosslinked to unit 7 is an anti-human albumin antibody, and is provided as a positive control antibody. The antibody crosslinked to unit 0 is a mutant variant of the antibody cross-linked to unit 7, in which CDR1 of the heavy chain and CDR3 of the light chain have each been replaced with a scrambled peptide sequence, and is provided as a negative control. Units 1, 3, and 5 are each crosslinked to 2 μg of an antibody that binds specifically to anti-pancreatic cancer-associated antigen. Units 2, 4, and 6 are each crosslinked to 2 μg of an antibody that binds specifically to anti-pancreatic cancer-associated antigen. Units 1, 3, and 5 are each crosslinked to 20 μg of an antibody that binds specifically to anti-pancreatic cancer-associated antigen.

An electrode transducer is positioned beneath the piezoelectric surface, and the piezoelectric surface is integrated on the surface of a 23G aspiration needle at the time the needle is manufactured. The electrode is connected to a processor via a wireless antenna. Thus, a fine-needle aspirator is produced.

Example 3

The fine-needle aspirator of Example 1 is fitted on the end of an endoscopic ultrasound probe. The fine-needle aspirator is attached to an endoscopic ultrasound probe as illustrated in FIG. 2A. The fine-needle aspirator and ultrasound are positioned in the liver of a patient for the purposes of collecting a biopsy. The probe is vibrated at a frequency of 10 MHz in pulses of 1 μs, and a baseline vibration frequency of each unit is determined. Unit 13 becomes saturated with LDH, producing a change in vibration frequency of unit 13. This changed vibration frequency is provided as a positive control. Luciferase is not present in the human tissue, and the antibodies of unit 0 remain unbound, and the vibration frequency of Unit 0 is used as a negative control An operator moves the probe through the liver of the patient, and the vibration frequency of each unit is monitored, and fit to a curve modeled on the negative and positive controls. The probe is positioned proximally to early stage hepatocellular carcinoma cells. The antibodies immobilized on units 1, 2, 5, 6, 9, and 10 bind to antigens of the carcinoma cells. A change in vibration frequency is observed for units 1, 2, 5, 6, 9, 10, and a processor produces an output as illustrated in FIG. 3, thus alerting the operator of binding of early-stage. A biopsy is taken from the region where the binding to units 1, 2, 5, 6, 9 and 10 is detected using the aspiration needle. The ultrasound probe is then withdrawn from the patient.

Example 4

The fine-needle aspirator of Example 2 is affixed to an endoscopic ultrasound probe as in Example 3. The probe is inserted into the pancreas of a patient. The probe is vibrated at 9 MHz in pulses of 0.5 μs. The antibodies of unit 7 bind to albumin, while the antibodies of unit 0 remain unbound, thus providing a change in the vibration frequency of unit 7, but not unit 0. The amount of change of vibration frequency is noted, and the probe is slowly moved through the pancreas. The probe is positioned near pancreatic cancer cells, and the antibodies of units 1-6 bind to PCCA on the surfaces of these cancer cells. The vibration frequency changes for units 1-6, and is compared to the change of vibration frequency of unit 7, and it is determined that units 1-6 are bound to their relevant antigen. While the probe is positioned in a region of interest that indicated binding of PCCA, a biopsy is taken using the aspiration needle, and the probe is withdrawn from the patient.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An endoscopic ultrasound probe comprising:
   a piezoelectric wafer;
   at least one antibody immobilized on the piezoelectric wafer;
   an electrode transducer on a needle, the piezoelectric wafer being stacked on the electrode transducer;
   the endoscopic ultrasound probe being configured to apply an ultrasound energy to the piezoelectric wafer to create a vibration in the piezoelectric wafer; and
   the electrode transducer being configured to detect an electrical signal generated by the piezoelectric wafer in response to the vibration in the piezoelectric wafer and transmit the detected electric signal to a recording device for the detection of a change in the vibration in the piezoelectric wafer due to binding of an antigen to the antibody immobilized on the piezoelectric wafer.

2. The endoscopic ultrasound probe of claim 1, wherein the piezoelectric wafer is crystalline.

3. The endoscopic ultrasound probe of claim 1, wherein the change in the vibration in the piezoelectric wafer due to binding of an antigen to the antibody immobilized on the piezoelectric wafer is a change in frequency of the vibration in the piezoelectric wafer.

4. The endoscopic ultrasound probe of claim 1, further comprising a processor, wherein the electrode is in data communication with the processor.

5. The endoscopic ultrasound probe of claim 1, wherein the at least one antibody-immobilized on the piezoelectric wafer comprises:
   at least a first antibody immobilized on a first area of the piezoelectric wafer; and
   at least a second antibody immobilized on a second area of the piezoelectric wafer.

6. The endoscopic ultrasound probe of claim 5, wherein the at least the first antibody specifically binds to a first antigen, and wherein the at least the second antibody specifically binds to a second antigen.

7. The endoscopic ultrasound probe of claim 6, wherein the first antigen comprises a first tissue-specific marker, and wherein the second antigen comprises a second tissue-specific marker.

8. The endoscopic ultrasound probe of claim 5, wherein the first area and second area are arranged in a systematic pattern on the piezoelectric wafer.

9. A method of detecting the presence of an antigen, the method comprising:
   providing an endoscopic ultrasound probe comprising:
      a piezoelectric wafer;
      a needle;
      an electrode transducer on the needle, the piezoelectric wafer being stacked on the electrode transducer; and
      at least one antibody immobilized on the piezoelectric wafer;
   stimulating the endoscopic ultrasound probe with at least one ultrasound wave to supply an ultrasound energy to the piezoelectric wafer to create a vibration in the piezoelectric wafer;
   detecting an electrical signal generated by the piezoelectric wafer in response to the vibration in the piezoelectric wafer;
   transmitting the detected electrical signal to a detecting device; and
   detecting a change in vibration of the piezoelectric wafer upon binding of an antigen to the at least one antibody.

10. The method of claim 9, wherein detecting a change in vibration comprises:
    determining a first vibration frequency of the piezoelectric wafer when no antigen is bound to the at least one antibody; and
    determining a second vibration frequency of the piezoelectric wafer when an antigen is bound to the at least one antibody.

11. The method of claim 9, wherein detecting a change in vibration comprises monitoring data in real time.

12. The method of claim 9, wherein the at least one antibody is configured to bind specifically to the tissue-specific antigen, the method further comprising binding the at least one antibody to a tissue-specific antigen.

13. The method of claim 9, wherein the at least one antibody immobilized on the piezoelectric wafer comprises:
    at least a first antibody immobilized on a first area of the piezoelectric wafer; and
    at least a second antibody immobilized on a second area of the piezoelectric wafer.

14. The method of claim 13, wherein the first antibody specifically binds to a tissue-specific antigen, and wherein the second antibody does not bind to the tissue-specific antigen, the method further comprising:
    binding the first antibody to a tissue-specific antigen;
    detecting a vibration frequency of the first area when the first antibody is bound to the tissue-specific antigen; and
    detecting a vibration frequency of the second area.

15. The method of claim 14, wherein detecting a vibration frequency of the second area occurs when the first antibody is bound to the tissue-specific antigen at the first area.

16. The method of claim 9, wherein the at least one antibody binds to an albumin, an albumin fragment, or lactose dehydrogenase (LDH).

17. An aspiration needle comprising:
   an electrode transducer on the aspiration needle;
   a piezoelectric wafer on the electrode transducer, the piezoelectric wafer being configured to vibrate in response to ultrasound energy; and
   at least one antibody on the piezoelectric wafer;
   wherein the aspiration needle is configured to fit on an endoscopic ultrasound probe; and
   wherein the electrode transducer is configured to detect an electrical signal generated by the piezoelectric wafer in response to the vibration in the piezoelectric wafer.

18. The aspiration needle of claim 17, wherein the at least one antibody binds specifically to an extracellular marker.

19. The aspiration needle of claim 17, wherein the at least one antibody comprises:
   a first antibody that binds specifically to a first antigen, wherein the first antibody is immobilized on a first area of the piezoelectric wafer; and
   a second antibody that binds specifically to a second antigen, wherein the second antibody is immobilized on a second area of the piezoelectric wafer.

20. The aspiration needle of claim 19, wherein the first area of the piezoelectric wafer and the second area of the piezoelectric wafer are positioned in a random pattern on a surface of the piezoelectric wafer.

21. The aspiration needle of claim 19, wherein the first area of the piezoelectric wafer and the second area of the piezoelectric wafer are positioned in an ordered array on a surface of the piezoelectric wafer.

22. The aspiration needle of claim 19, wherein the at least one antibody further comprises a third antibody configured to bind specifically to the first antigen, wherein the third antibody is immobilized on a third area of the piezoelectric wafer.

23. The aspiration needle of claim 19, further comprising an electrical lead in electrical communication with the electrode transducer.

24. A kit comprising:
   at least one aspirator needle;
   at least one ultrasound transducer configured to attach to a surface of the aspirator needle;
   at least one piezoelectric wafer configured to attach to a surface of the ultrasound transducer and to vibrate in response to ultrasound energy;
   at least one antibody;
   wherein the at least one ultrasound transducer is configured to supply ultrasound energy to the at least one piezoelectric wafer, the ultrasound transducer being configured to detect an electrical signal generated by the piezoelectric wafer in response to the vibration in the piezoelectric wafer.

25. The kit of claim 24, wherein the at least one antibody is immobilized on the at least one piezoelectric wafer.

* * * * *